United States Patent
Goto et al.

(10) Patent No.: US 11,978,208 B2
(45) Date of Patent: May 7, 2024

(54) TRAINED MODEL, LEARNING METHOD, LEARNING PROGRAM, MEDICAL INFORMATION ACQUISITION DEVICE, MEDICAL INFORMATION ACQUISITION METHOD, AND MEDICAL INFORMATION ACQUISITION PROGRAM

(71) Applicant: FUJIFILM Corporation, Tokyo (JP)

(72) Inventors: Tsubasa Goto, Tokyo (JP); Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 357 days.

(21) Appl. No.: 17/388,022

(22) Filed: Jul. 29, 2021

(65) Prior Publication Data

US 2021/0358126 A1    Nov. 18, 2021

Related U.S. Application Data

(63) Continuation of application No. PCT/JP2020/002926, filed on Jan. 28, 2020.

(30) Foreign Application Priority Data

Jan. 31, 2019   (JP) ................................ 2019-016037

(51) Int. Cl.
*G06T 7/00*     (2017.01)
*G06N 20/00*    (2019.01)
(Continued)

(52) U.S. Cl.
CPC .......... *G06T 7/0016* (2013.01); *G06N 20/00* (2019.01); *G16H 10/20* (2018.01); *G16H 10/40* (2018.01); *G16H 10/60* (2018.01); *G16H 15/00* (2018.01); *G16H 30/20* (2018.01); *G16H 30/40* (2018.01); *G16H 50/20* (2018.01); *G16H 50/30* (2018.01);
(Continued)

(58) Field of Classification Search
CPC ......... G06N 20/00; G06T 7/0016; G06T 7/00; G16H 30/40; G16H 30/20; G16H 10/60; G16H 50/50; G16H 50/20; G16H 50/70; G16H 10/40; G16H 10/20; G16H 50/30; G16H 15/00
See application file for complete search history.

(56) References Cited

U.S. PATENT DOCUMENTS

| | | | |
|---|---|---|---|
| 7,912,528 | B2 | 3/2011 | Krishnan et al. |
| 2016/0061917 | A1 | 3/2016 | Chase et al. |
| 2020/0054266 | A1 | 2/2020 | Hirobe |

FOREIGN PATENT DOCUMENTS

| | | |
|---|---|---|
| EP | 0879449 | 11/1998 |
| EP | 3404666 | 11/2018 |

(Continued)

OTHER PUBLICATIONS

"Search Report of Europe Counterpart Application", dated Aug. 10, 2022, pp. 1-13.

(Continued)

*Primary Examiner* — Tuan H Nguyen
(74) *Attorney, Agent, or Firm* — JCIPRNET

(57) ABSTRACT

There is provided a medical information acquisition device including an information acquisition unit that acquires functional change information obtained on the basis of a reference image and a past image acquired by capturing images of the same subject at a reference time and a past time closer to the past than the reference time, respectively, using a trained model.

19 Claims, 12 Drawing Sheets

(51) Int. Cl.
  *G16H 10/20* (2018.01)
  *G16H 10/40* (2018.01)
  *G16H 10/60* (2018.01)
  *G16H 15/00* (2018.01)
  *G16H 30/20* (2018.01)
  *G16H 30/40* (2018.01)
  *G16H 50/20* (2018.01)
  *G16H 50/30* (2018.01)
  *G16H 50/50* (2018.01)
  *G16H 50/70* (2018.01)
  *A61B 10/00* (2006.01)
  *G16H 20/70* (2018.01)

(52) U.S. Cl.
  CPC ............ *G16H 50/50* (2018.01); *G16H 50/70* (2018.01); *A61B 2010/0077* (2013.01); *G06T 2207/10081* (2013.01); *G06T 2207/10088* (2013.01); *G06T 2207/20081* (2013.01); *G06T 2207/30016* (2013.01); *G16H 20/70* (2018.01)

(56) References Cited

FOREIGN PATENT DOCUMENTS

| EP | 3550503 | 10/2019 |
|---|---|---|
| JP | 2007527743 | 10/2007 |
| JP | 2008065836 | 3/2008 |
| JP | 2018038515 | 3/2018 |
| JP | 2018061440 | 4/2018 |
| JP | 2018529474 | 10/2018 |
| WO | 2018100797 | 6/2018 |
| WO | 2018211696 | 11/2018 |

OTHER PUBLICATIONS

Md. Shafiul Islam et al., "Analysis of Morphological Brain Change of Alzheimer Disease (AD) Patients," Applied Physics Research, vol. 2, Nov. 2010, pp. 148-155.

Ramon Casanova et al., "Alzheimer's Disease Risk Assessment Using Large-Scale Machine Learning Methods," Journal.pone. 0077949, vol. 8, Nov. 2013, pp. 1-13.

Saman Sarraf et al., "DeepAD: Alzheimer's Disease Classification via Deep Convolutional Neural Networks using MRI and fMRI,", Aug. 2016, pp. 1-15. Available at: https://doi.org/10.1101/070441.

Shangran Qiu et al., "Fusion of deep learning models of MRI scans, Mini-Mental State Examination, and logical memory test enhances diagnosis of mild cognitive impairment," Alzheimer s & Dementia Diagnosis Assessment & Disease Monitoring, Sep. 2018, pp. 737-749.

"International Search Report (Form PCT/ISA/210) of PCT/JP2020/002926," dated Apr. 7, 2020, with English translation thereof, pp. 1-5.

"Written Opinion of the International Searching Authority (Form PCT/ISA/237)" of PCT/JP2020/002926, dated Apr. 7, 2020, with English translation thereof, pp. 1-11.

"Office Action of Japan Counterpart Application", dated Jul. 5, 2022, with English translation thereof, pp. 1-6.

FIG. 5
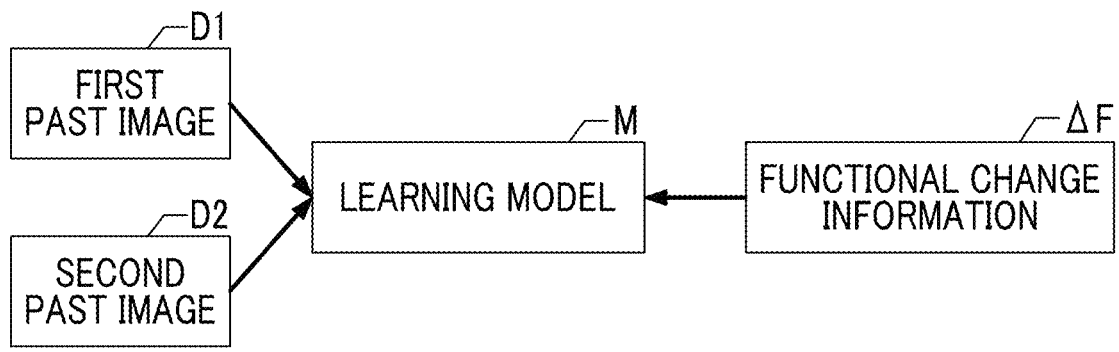
FIG. 6
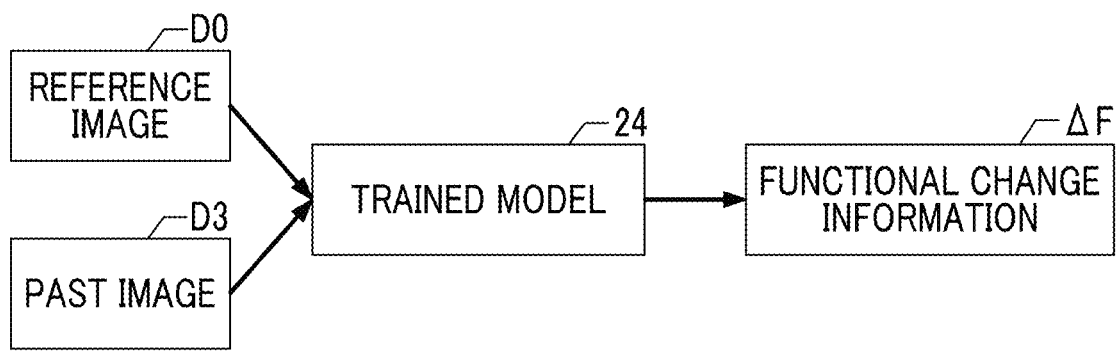
FIG. 7
| F3 (F0 + ΔF) | PREDICTION RESULT |
|---|---|
| 0 TO 10 POINTS | SEVERE DEMENTIA |
| 11 TO 20 POINTS | INTERMEDIATE DEMENTIA |
| 21 TO 23 POINTS | MILD DEMENTIA |
| 24 TO 30 POINTS | NORMAL |

TRAINED MODEL, LEARNING METHOD, LEARNING PROGRAM, MEDICAL INFORMATION ACQUISITION DEVICE, MEDICAL INFORMATION ACQUISITION METHOD, AND MEDICAL INFORMATION ACQUISITION PROGRAM

CROSS-REFERENCE TO RELATED APPLICATIONS

This application is a continuation application of International Application No. PCT/JP2020/002926 filed Jan. 28, 2020 the disclosure of which is incorporated herein by reference in its entirety. Further, this application claims priorities from Japanese Patent Application No. 2019-016037, filed Jan. 31, 2019, the disclosure of which is incorporated herein by reference in their entirety.

TECHNICAL FIELD

The present disclosure relates to a trained model, a learning method, a learning program, a medical information acquisition device, a medical information acquisition method, and a medical information acquisition program.

RELATED ART

In recent years, advances in medical apparatuses, such as a computed tomography (CT) apparatus and a magnetic resonance imaging (MRI) apparatus, have made it possible to perform image diagnosis using high-resolution medical images with higher quality. In particular, since a lesion region can be accurately specified by image diagnosis using CT images, MRI images, and the like, an appropriate treatment is performed on the basis of the specification result. In addition, there is a technique which analyzes a medical image with computer-aided diagnosis (CAD) using a discriminator trained by deep learning and the like, extracts the region, position, volume, and the like of a lesion included in the medical image, and acquires the extracted results as analysis results. For example, JP2007-527743A discloses a method which automatically evaluates the state of the heart using a CAD system on the basis of information including features from image data of the heart of the patient and information including features from non-image data records, such as clinical information of the patient, and supports the workflow of the doctor related to treatment pathways for the patient.

On the other hand, in recent years, with the advent of an aging society, the number of patients with dementia diseases has increased year by year. Dementia develops in a case in which the atrophy of the brain progresses due to the accumulation of a protein called amyloid beta in the brain and cognitive ability is reduced. Treatments for dementia are being studied, but there is still no cure for dementia. Therefore, it is important to detect the atrophy of the brain in its early stages and to start a treatment to slow down the progression of dementia in its early stages in order to maintain the quality of life.

In recent years, information related to the state of the brain can be acquired by nuclear medicine examinations, such as single photon emission computed tomography (SPECT) and positron emission tomography (PET), CT images acquired by a CT apparatus, and MRI images acquired by an MRI apparatus in order to meet the demands. For example, a reduction in the blood flow and metabolism of a local part of the brain can be detected by seeking a change in the local part of the brain over time using SPECT and PET images. Further, in recent years, the relationship between the degree of atrophy of the brain and the degree of progression of dementia has been studied. For example, Analysis of Morphological Brain Change of Alzheimer Disease (AD) Patients., Islam, M., Alam, S., Ferdousy, R., Chowdhury, E., November 2010, Applied Physics Research, Vol. 2, No. 2, 148-155 discloses a study on the relationship between Alzheimer-type dementia and the brain. In addition, Alzheimer's disease risk assessment using large-scale machine learning methods, Casanova, R., Hsu, F C, Sink, K M, Rapp, S R, Williamson, J D, Resnick, S M et al., Nov. 8, 2013; 8(11):e77949. doi: 10.1371/journal.pone.0077949 discloses a study on an Alzheimer-type dementia risk evaluation index using machine learning.

The atrophy of the brain can be detected by calculating the volume of a specific part of the brain using MRI images and comparing a change in the volume over time. For example, Deep A D: Alzheimer's Disease Classification via Deep Convolutional Neural Networks using MRI and fMRI, Saman Sarrafa et al., first posted online Aug. 21, 2016; doi: http://dx.doi.org/10.1101/070441 proposes a method which automatically discriminates a normal brain image and a dementia brain image using machine learning.

For various diseases including dementia, it is desirable that the degree of progression of the diseases is predicted to support diagnosis by the doctor, in order to select the best treatment method at the present time such as a treatment method for slowing down the progression of the diseases. However, JP2007-527743A, Analysis of Morphological Brain Change of Alzheimer Disease (AD) Patients., Islam, M., Alam, S., Ferdousy, R., Chowdhury, E., November 2010, Applied Physics Research, Vol. 2, No. 2, 148-155, Alzheimer's disease risk assessment using large-scale machine learning methods, Casanova, R., Hsu, F C, Sink, K M, Rapp, S R, Williamson, J D, Resnick, S M et al., Nov. 8, 2013; 8(11):e77949. doi: 10.1371/journal.pone.0077949, and Deep A D: Alzheimer's Disease Classification via Deep Convolutional Neural Networks using MRI and fMRI, Saman Sarrafa et al., first posted online Aug. 21, 2016; doi: http://dx.doi.org/10.1101/070441 do not disclose any technique that predicts the degree of progression of diseases.

SUMMARY

An object of the present disclosure is to provide a technique that predicts the degree of progression of diseases to support diagnosis.

According to a first aspect of the present disclosure, there is provided a trained model that has been trained to receive image information as an input and to output functional change information using, as training data, learning information including a plurality of information sets each of which includes: the image information based on a first past image acquired by capturing an image of a subject at a first time and a second past image acquired by capturing an image of the subject at a second time closer to the present than the first time; and functional change information that indicates a change in a function of the subject over time and is based on first past functional information acquired by examining the function of the subject at the second time and second past functional information acquired by examining the function of the subject at a third time closer to the present than the second time.

According to a fourteenth aspect of the present disclosure, there is provided a method for training a learning model. The method comprises: acquiring a plurality of information sets each of which includes image information based on a first past image acquired by capturing an image of a subject at a first time and a second past image acquired by capturing an image of the subject at a second time closer to the present than the first time and functional change information that indicates a change in a function of the subject over time and is based on first past functional information acquired by examining the function of the subject at the second time and second past functional information acquired by examining the function of the subject at a third time closer to the present than the second time; and training the learning model, using learning information including the plurality of acquired information sets as training data, to receive the image information as an input and to output the functional change information.

According to a fifteenth aspect of the present disclosure, there is provided a program for training a learning model. The program causes a computer to perform: acquiring a plurality of information sets each of which includes image information based on a first past image acquired by capturing an image of a subject at a first time and a second past image acquired by capturing an image of the subject at a second time closer to the present than the first time and functional change information that indicates a change in a function of the subject over time and is based on first past functional information acquired by examining the function of the subject at the second time and second past functional information acquired by examining the function of the subject at a third time closer to the second time; and training the learning model, using learning information including the plurality of acquired information sets as training data, to receive the image information as an input and to output the functional change information.

Another first medical information acquisition device according to the present disclosure comprises: a memory that stores commands to be executed by a computer; and a processor configured to execute the stored commands. The processor performs a process of acquiring functional change information obtained on the basis of a reference image and a past image acquired by capturing images of the same subject at a reference time and a past time closer to the past than the reference time, respectively, using the above-described trained model.

Another second medical information acquisition device according to the present disclosure comprises: a memory that stores commands to be executed by a computer; and a processor configured to execute the stored commands. The processor performs a process of acquiring functional change information obtained on the basis of a reference image and a past image acquired by capturing images of the same subject at a reference time and a past time closer to the past than the reference time, respectively, and reference biological information and past biological information acquired by biopsy on the same subject at the reference time and the past time, respectively, using the above-described trained model.

BRIEF DESCRIPTION OF THE DRAWINGS

FIG. 5 is a diagram illustrating a method for training a learning model.

FIG. 6 is a diagram illustrating the acquisition of functional change information by an information acquisition unit according to the first embodiment of the present disclosure.

FIG. 7 is a diagram illustrating the prediction of the degree of progression of dementia.

DETAILED DESCRIPTION

Figure 1:
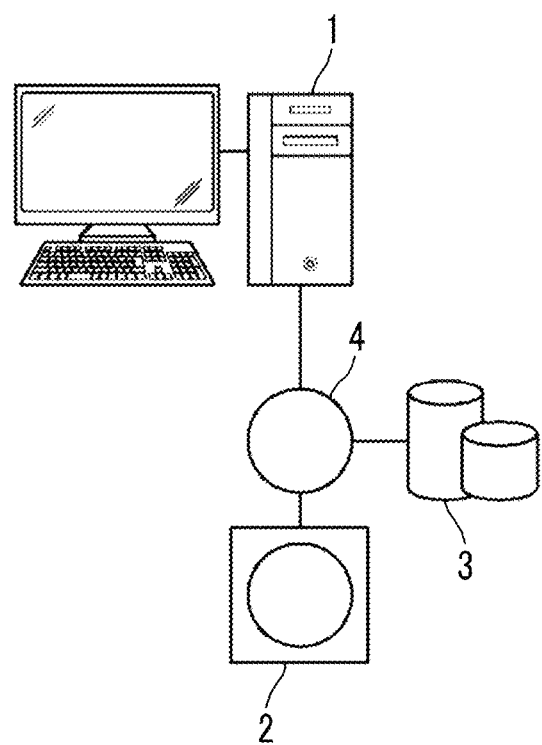
FIG. 1 is a hardware configuration diagram illustrating the outline of a diagnosis support system to which a medical information acquisition device according to an embodiment of the present disclosure is applied.

Hereinafter, embodiments of the present disclosure will be described with reference to the drawings. FIG. 1 is a hardware configuration diagram illustrating the outline of a diagnosis support system to which a medical information acquisition device according to an embodiment of the present disclosure is applied. As illustrated in FIG. 1, in the diagnosis support system, a medical information acquisition device 1, a three-dimensional imaging apparatus 2, and an image storage server 3 according to this embodiment are connected through a network 4 such that they can communicate with each other.

The three-dimensional imaging apparatus 2 is an apparatus that captures an image of a diagnosis target part of a subject to generate a three-dimensional image indicating the part and is specifically a CT apparatus, an MRI apparatus, a PET apparatus, or the like. The three-dimensional image which consists of a plurality of slice images and has been generated by the three-dimensional imaging apparatus 2 is transmitted and stored in the image storage server 3 for each unit examination. In addition, in this embodiment, the diagnosis target part of the patient who is a subject is the brain, and the three-dimensional imaging apparatus 2 is an MRI apparatus. Then, the MRI apparatus generates a three-dimensional MRI image including the brain of the subject.

In this embodiment, the MRI image is a diffusion-weighted image. Further, in this embodiment, the MRI image is used. However, the technology of the present disclosure is not limited to the MRI image. For example, a CT image acquired by a CT apparatus may be used. In this case, a non-contrast-enhanced CT image acquired by performing imaging without using a contrast medium or a contrast-enhanced CT image acquired by performing imaging using a contrast medium may be used as the CT image.

The image storage server 3 is a computer that stores and manages various types of data and comprises a high-capacity external storage device and database management software. The image storage server 3 performs communication with other apparatuses through the wired or wireless network 4 to transmit and receive, for example, image data. Specifically, the image storage server 3 acquires various types of data including the image data of the three-dimensional image generated by the three-dimensional imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM).

The medical information acquisition device 1 is implemented by installing a learning program and a medical information acquisition program according to the present disclosure in a computer. The computer may be a workstation or a personal computer that is directly operated by a doctor who performs diagnosis or may be a server computer that is connected to them through the network. The learning program and the medical information acquisition program are recorded on a recording medium, such as a digital versatile disc (DVD) or a compact disc read only memory (CD-ROM), is distributed, and is installed in the computer from the recording medium. Alternatively, the learning program and the medical information acquisition program are stored in a storage device of a server computer connected to the network or a network storage so as to be accessed from the outside, are downloaded to the computer used by the doctor on request, and are then installed in the computer.

Figure 2:
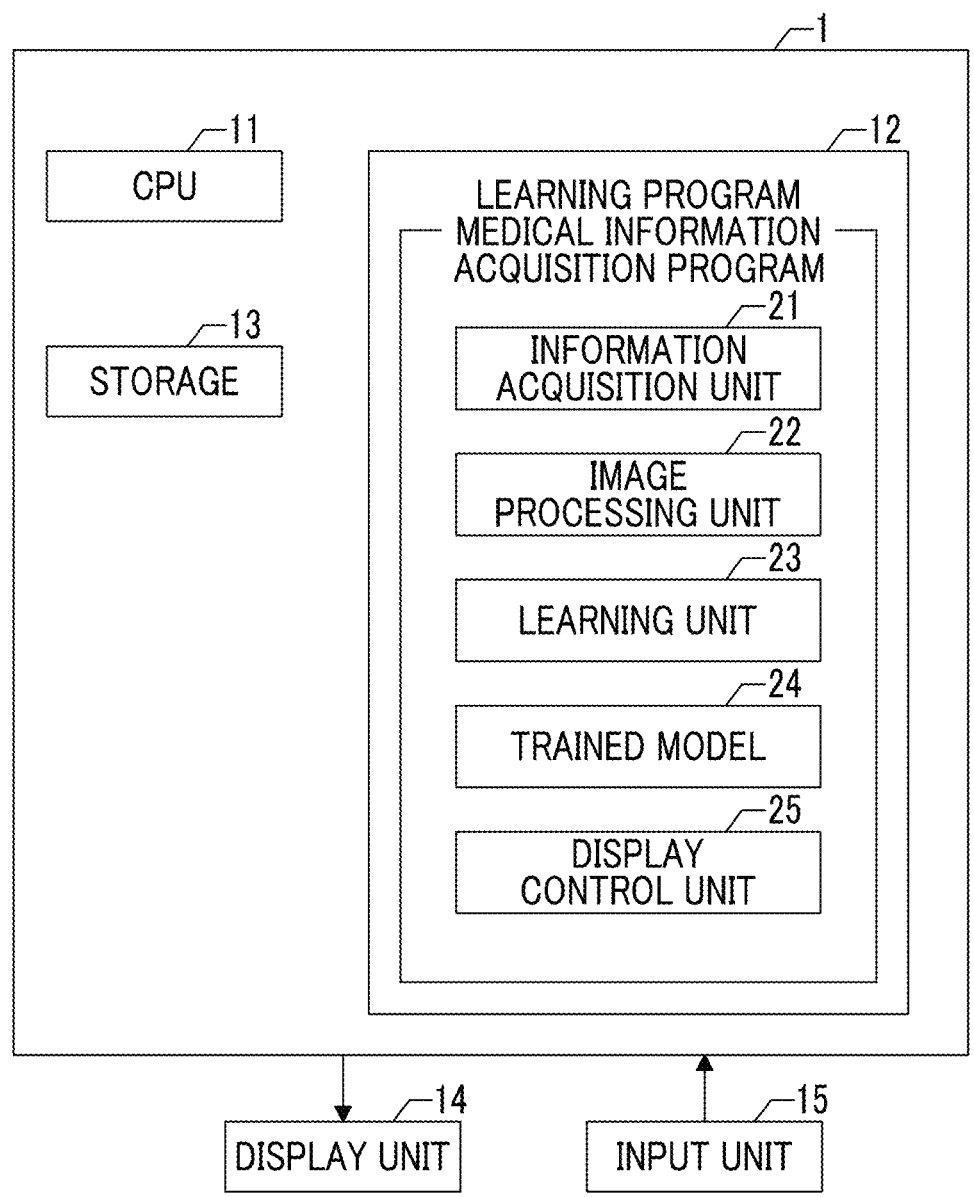
FIG. 2 is a block diagram schematically illustrating the configuration of a medical information acquisition device according to a first embodiment of the present disclosure.

FIG. 2 is a diagram schematically illustrating the configuration of the medical information acquisition device according to an embodiment of the present disclosure which is implemented by installing the learning program and the medical information acquisition program in the computer. As illustrated in FIG. 2, the medical information acquisition device 1 comprises a central processing unit (CPU) 11, a memory 12, and a storage 13 as the configuration of a standard workstation. In addition, a display unit 14 consisting of, for example, a liquid crystal display and an input unit 15 consisting of, for example, a keyboard and a mouse are connected to the medical information acquisition device 1. The input unit 15 receives various setting inputs from the user. In addition, a touch panel may be used so as to function as both the display unit 14 and the input unit 15.

The storage 13 consists of, for example, a hard disk drive and a solid state drive (SSD). The storage 13 stores various kinds of information including the medical images of the subject and information required for processes which are acquired from the image storage server 3 through the network 4. In this embodiment, a score acquired by a psychological examination for dementia is stored as functional information acquired by examining the function of the subject at the time of capturing each medical image. In this embodiment, specifically, as the score, points acquired by the patient checking in a checklist for evaluating the degree of dementia, such as Mini-Mental State Examination (MMSE), Alzheimer's Disease Assessment Scale (ADAS), or Hasegawa Dementia Scale, are stored. In this embodiment, the examination result of the MMSE is stored as the score. However, the technology of the present disclosure is not limited thereto, and any score may be used as long as it can evaluate the degree of dementia.

Further, the memory 12 stores the learning program and the medical information acquisition program. The learning program is a learning program that trains a learning model M which will be described below and defines the following processes as the processes to be performed by the CPU 11: an information acquisition process of acquiring a plurality of information sets, each of which includes image information based on a first past image acquired by capturing an image of a subject at a first time and a second past image acquired by capturing an image of the subject at a second time closer to the present than the first time and functional change information that indicates a change in a function of the subject over time and is based on first past functional information acquired by examining the function of the subject at the second time and second past functional information acquired by examining the function of the subject at a third time closer to the present than the second time; and a learning process of training the learning model, using learning information including the plurality of acquired information sets as training data, so as to receive the image information as an input and to output the functional change information.

Further, the medical information acquisition program defines the following process as the process to be performed by the CPU 11: an information acquisition process of acquiring functional change information obtained on the basis of a reference image and a past image acquired by capturing images of the same subject at a reference time and a past time closer to the past than the reference time, respectively, using a trained model 24 trained by the learning program. In addition, the medical information acquisition program defines, as the process to be performed by the CPU 11, image processing that performs at least one of a density normalization process or a registration process on the reference image and the past image.

Then, the CPU 11 performs these processes according to the programs such that the computer functions as an information acquisition unit 21, an image processing unit 22, a learning unit 23, the trained model 24, and a display control unit 25.

Figure 3:
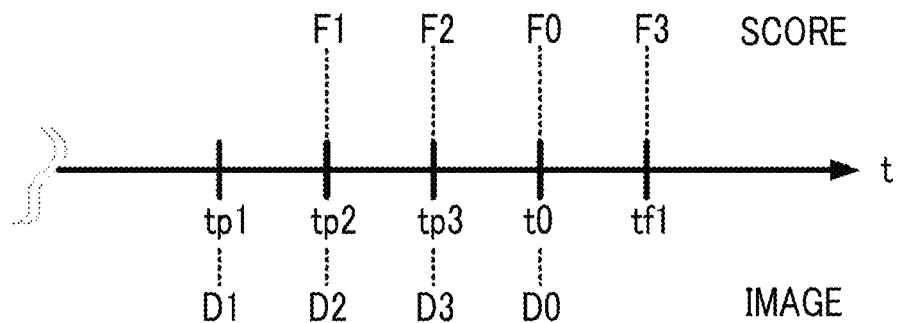
FIG. 3 is a diagram illustrating a time series of information acquisition.

The information acquisition unit 21 acquires, as the training data, learning information including a plurality of information sets, each of which includes the image information and the functional change information, in order to train the learning model M which will be described below. Here, FIG. 3 is a diagram illustrating a time series of information acquisition. As illustrated in FIG. 3, a first past image D1 and a second past image D2 which are the MRI images of the brain of the subject acquired by capturing the images of the same subject at a first time tp1 and a second time tp2 closer to the present than the first time tp1 are acquired as the image information from the image storage server 3. In addition, in a case in which the first past image D1 and the second past image D2 have already been stored in the storage 13, the information acquisition unit 21 may acquire the first past image D1 and the second past image D2 from the storage 13. Further, the information acquisition unit 21 acquires the first past images D1 and the second past images D2 of a large number of subjects in order to train the learning model M which will be described below.

Further, the information acquisition unit 21 acquires, from the storage 13, a first score F1 and a second score F2 as the scores acquired by examining the function of the subject, of which the first past image D1 and the second past image D2 were captured, at the second time tp2 and a third time tp3 closer to the present than the second time tp2. Furthermore, for example, in a case in which the first score F1 and the second score F2 have been stored as accessory information of the past images captured at the time when each score was acquired in the image storage server 3 so as to be attached to the past images, the information acquisition unit 21 may acquire the first score F1 and the second score F2 from the image storage server 3. In addition, the information acquisition unit 21 acquires the first scores F1 and the second scores F2 for a large number of subjects in order to train the learning model M which will be described below.

Further, the information acquisition unit 21 acquires, from the image storage server 3, a reference image D0 and a past image D3 acquired by capturing the images of the same subject at a reference time t0 and a past time closer to the past than the reference time t0, for example, at the third time tp3, respectively. In addition, in a case in which the reference image D0 and the past image D3 have already been stored in the storage 13, the information acquisition unit 21 may acquire the reference image D0 and the past image D3 from the storage 13. In this embodiment, the reference time t0 is the current time, that is, the time when the latest image of the subject was acquired, and the image acquired at this time is referred to as the reference image D0.

Further, the information acquisition unit 21 acquires functional change information $\Delta F$ obtained on the basis of the first past image D1 and the second past image D2 and functional change information $\Delta F$ obtained on the basis of the reference image D0 and the past image D3. Furthermore, as illustrated in FIG. 3, the functional change information $\Delta F$ is the amount of change in the value of the second score F2 acquired at the third time tp3 with respect to the value of the first score F1 acquired at the second time tp2 and the amount of change in the value of a future score F3 that is predicted to be acquired at a future time tfl closer to the future than the reference time t0 with respect to the value of a reference score F0 acquired at the reference time t0. A method for acquiring the functional change information $\Delta F$ will be described in detail below. In addition, the information acquisition unit 21 acquires, as the future score F3, a score obtained by adding the acquired functional change information $\Delta F$ to the reference score F0.

Figure 4:
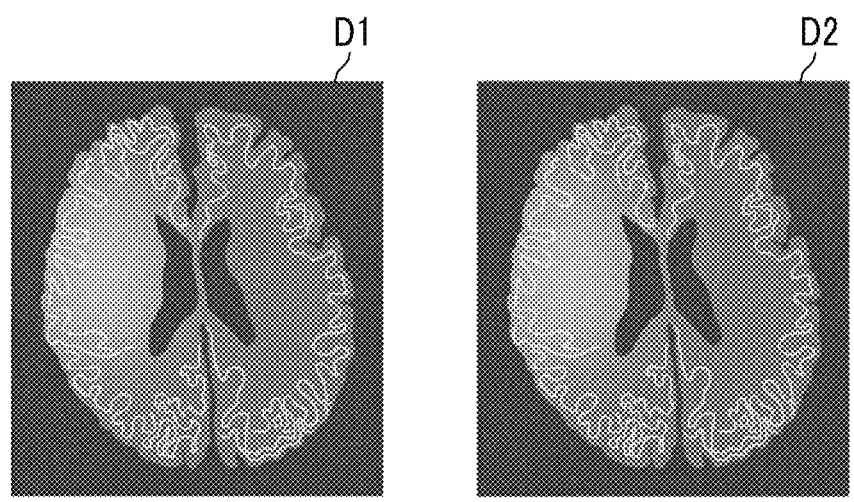
FIG. 4 is a diagram illustrating image processing by an image processing unit according to the first embodiment of the present disclosure.

The image processing unit 22 performs the density normalization process and the registration process on the first past images D1 and the second past images D2 of a large number of subjects acquired by the information acquisition unit 21, and the reference image D0 and the past image D3 of the subject for which the degree of progression of dementia is predicted. FIG. 4 is a diagram illustrating image processing by the image processing unit 22. Further, in FIG. 4, both the first past image D1 and the second past image D2 are three-dimensional MRI images. However, here, for the sake of explanation, a two-dimensional tomographic image in one tomographic plane corresponding to each MRI image is used.

As illustrated in FIG. 4, for the same subject, the shapes of the brains in the first past image D1 and the second past image D2 are substantially the same. Therefore, any one of the first past image D1 or the second past image D2 is registered with respect to the other image by rigid registration. In this embodiment, the second past image D2 is registered with respect to the first past image D1. However, the first past image D1 may be registered with respect to the second past image D2. In addition, non-rigid registration may be used as the registration. As the non-rigid registration, for example, a method may be used which non-linearly converts a feature point in the first past image D1 into a corresponding point corresponding to a feature point in the second past image D2, using a function such as a B-spline and a thin plate spline. However, the present disclosure is not limited thereto.

Further, the image processing unit 22 normalizes the density value of each pixel constituting each of the first past image D1 and the second past image D2. Specifically, for example, there is a process which multiplies the density value of each pixel by a coefficient such that any one of the maximum value, the average value, or the intermediate value of the density value in each image is set to the same value. Furthermore, the normalization process is not limited to the above, and a known method may be used.

The image processing unit 22 performs the density normalization process and the registration process on the first past image D1 and the second past image D2, similarly to the reference image D0 and the past image D3. The performance of the density normalization process and the registration process makes it possible to easily learn a change in the shape of the brain over time.

The learning unit 23 trains the learning model M using, as the training data, learning information including a plurality of information sets, each of which includes image information that is information of a set of images consisting of the first past image D1 and the second past image D2 and the functional change information $\Delta F$ that is information indicating a change in the first score F1 and the second score F2 over time so as to receive the image information as an input and to output the functional change information $\Delta F$.

FIG. 5 is a diagram illustrating a method for training the learning model M. Specifically, as illustrated in FIG. 5, the learning unit 23 inputs the first past image D1 and the second past image D2, and the functional change information $\Delta F$ which is the amount of change in the value of the second score F2 with respect to the value of the first score F1 as the training data to the learning model M to train the learning model M, that is, to perform machine learning. The learning is performed in this way to generate the trained model 24 that receives, as an input, the image information acquired by capturing the images of the same subject at different times and obtains the functional change information $\Delta F$. The trained model 24 learns change information between the first past image D1 and the second past image D2 as a feature.

In addition, for example, a support vector machine (SVM), a deep neural network (DNN), a convolutional neural network (CNN), and a recurrent neural network (RNN) can be used as a machine learning method.

FIG. 6 is a diagram illustrating the acquisition of the functional change information $\Delta F$ by the information acquisition unit 21 according to a first embodiment of the present disclosure. As illustrated in FIG. 6, the information acquisition unit 21 acquires the functional change information $\Delta F$ output from the trained model 24 in a case in which the reference image D0 and the past image D3 are input to the trained model 24 trained as described above, that is, the amount of change in the value of the future score F3 with respect to the value of the reference score F0. In addition, the information acquisition unit 21 acquires, as the future score F3, a score obtained by adding the acquired functional change information $\Delta F$ to the reference score F0.

FIG. 7 is a diagram illustrating the prediction of the degree of progression of dementia. In this embodiment, the psychological examination for dementia used to acquire the score F is the MMSE. The MMSE consists of 11 questions out of 30 points and covers, for example, orientation, memory, calculation, linguistic ability, and graphic ability. In the MMSE, generally, in a case in which the score is equal to or greater than 24, the subject is diagnosed as being normal. In a case in which the score is equal to or greater than 0 and equal to or less than 10, the subject is diagnosed as being likely to have severe dementia. In a case in which the score is equal to or greater than 11 and equal to or less than 20, the subject is diagnosed as being likely to have intermediate dementia. In a case in which the score is equal to or greater than 21 and equal to or less than 23, the subject is diagnosed as being likely to have mild dementia. That is, as illustrated in FIG. 7, in a case in which the future score F3, that is, the value obtained by adding the functional change information ΔF to the reference score F0 is equal to or greater than 0 and equal to or less than 10, it is predicted that the subject will have severe dementia. In a case in which the future score F3 is equal to or greater than 11 and equal to or less than 20, it is predicted that the subject will have intermediate dementia. In a case in which the future score F3 is equal to or greater than 21 and equal to or less than 23, it is predicted that the subject will have mild dementia. In a case in which the future score F3 is equal to or greater than 24 and equal to or less than 30, it is predicted that the subject will be normal.

The display control unit 25 displays, on the display unit 14, letter information of the prediction result of the progression of dementia, specifically, "the subject is likely to have severe dementia", "the subject is likely to have intermediate dementia", "the subject is likely to have mild dementia", "the subject is normal", and the like. Further, in this embodiment, the prediction result is displayed on the display unit 14. However, the technology of the present disclosure is not limited thereto. For example, the prediction result may be notified not by the display unit 14 but by a notification unit (not illustrated). Here, in the present disclosure, the "notification unit" means, for example, a voice reproduction device that outputs voice to audibly display the prediction result, a printer that records the prediction result on a recording medium, such as paper, to permanently display the prediction result in a visible manner, a communication unit, such as e-mail or a telephone, or an indicating light. At least two or more of the display unit 14, the voice reproduction device, the printer, the communication unit, and the indicating light may be combined and used.

Figure 8:
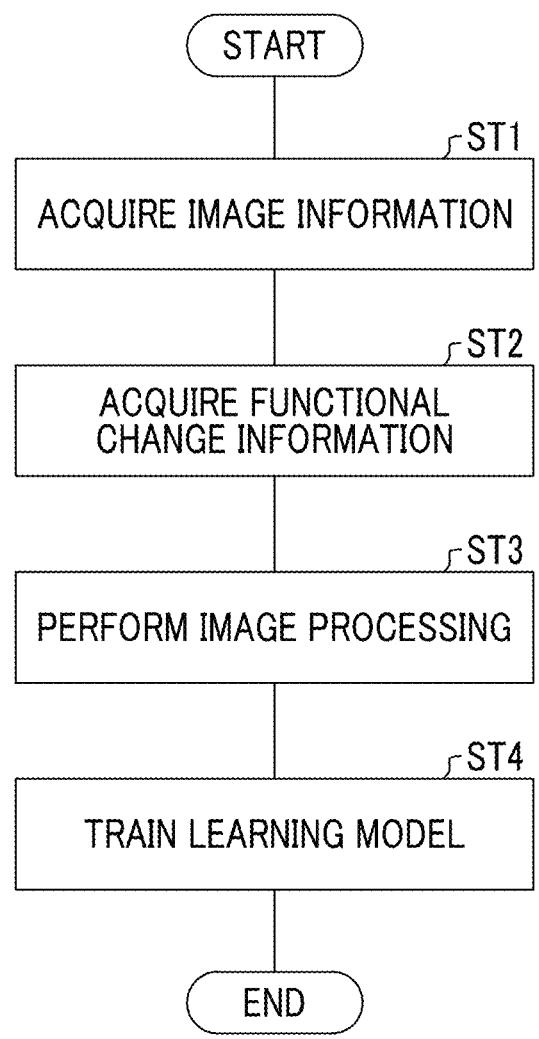
FIG. 8 is a flowchart illustrating the method for training the learning model performed in the first embodiment of the present disclosure.

Next, a process performed in this embodiment will be described. FIG. 8 is a flowchart illustrating the method for training the learning model in the first embodiment of the present disclosure. First, the information acquisition unit 21 acquires image information which is information of a set of images consisting of the first past image D1 and the second past image D2 (Step ST1). In addition, the information acquisition unit 21 acquires the first score F1 and the second score F2 and acquires the functional change information ΔF which is information indicating a change in the first score F1 and the second score F2 over time (Step ST2).

Then, the image processing unit 22 performs image processing including the density normalization process and the registration process on the first past image D1 and the second past image D2 (Step ST3). Then, the learning unit 23 trains the learning model M using, as the training data, the image information which is the information of a set of images consisting of the first past image D1 and the second past image D2 and the functional change information ΔF which is the amount of change in the value of the second score F2 with respect to the value of the first score F1 so as to receive the image information as an input and to output the functional change information ΔF (Step ST4). Then, the process ends.

Further, in this embodiment, each process is performed according to the procedure illustrated in the flowchart of FIG. 8. However, the technology of the present disclosure is not limited thereto. For example, the process of acquiring the functional change information ΔF in Step ST2 may be performed before the process of acquiring the image information in Step ST1, or the image processing in Step ST3 may be performed before the process of acquiring the functional change information ΔF in Step ST2.

Figure 9:
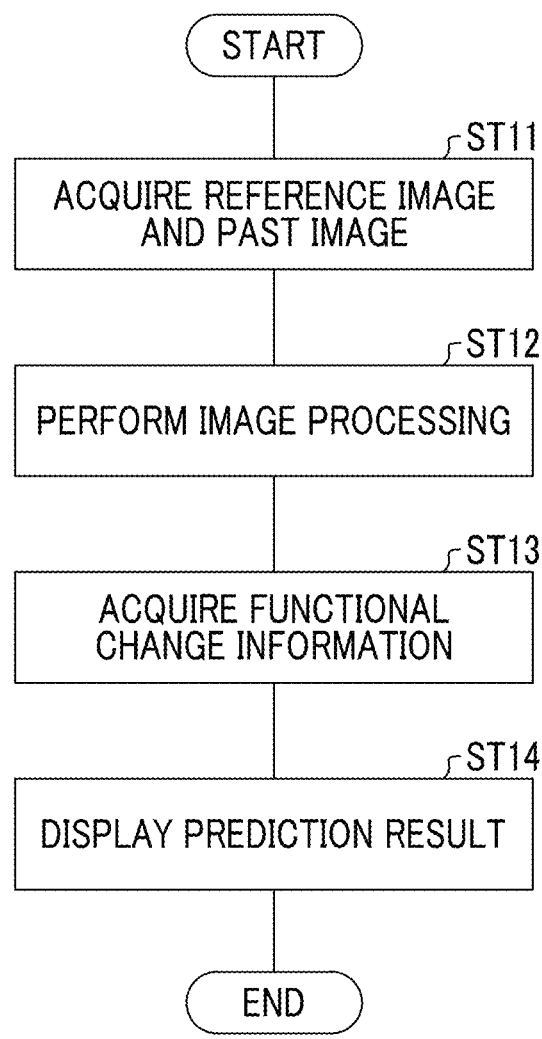
FIG. 9 is a flowchart illustrating a process performed in the first embodiment of the present disclosure.

FIG. 9 is a flowchart illustrating the process performed in the first embodiment of the present disclosure. First, the information acquisition unit 21 acquires the reference image D0 and the past image D3 (Step ST11), and the image processing unit 22 performs image processing including the density normalization process and the registration process on the reference image D0 and the past image D3 (Step ST12).

Then, the information acquisition unit 21 acquires the amount of change in the value of the future score F3 with respect to the value of the reference score F0 output from the trained model 24 in a case in which the reference image D0 and the past image D3 are input to the trained model 24, that is, the functional change information ΔF (Step ST13). In addition, the information acquisition unit 21 acquires a score obtained by adding the acquired functional change information ΔF to the reference score F0 as the future score F3, and the display control unit 25 displays the prediction result of the degree of progression of dementia corresponding to the value of the future score F3 illustrated in FIG. 7 on the display unit (Step ST14). Then, the process ends.

As described above, in this embodiment, the functional change information ΔF obtained on the basis of the reference image D0 and the past image D3 is acquired by the trained model 24 trained using, as the training data, the learning information including a plurality of information sets, each of which includes the image information based on the first past image D1 and the second past image D2 and the functional change information ΔF that indicates a change in the function of the subject over time and is based on the first score F1 and the second score F2 so as to receive the image information as an input and to output the functional change information ΔF. The acquisition of the functional change information ΔF makes it possible to acquire the score obtained by adding the acquired functional change information ΔF to the reference score F0 as the future score F3. Therefore, the degree of progression of dementia can be predicted to support the diagnosis of dementia.

In addition, in this embodiment, the density normalization process and the registration process are performed on the first past image D1 and the second past image D2, and the reference image D0 and the past image D3. However, the technology of the present disclosure is not limited thereto. Only the density normalization process may be performed, or only the registration process may be performed. Further, the density normalization process and the registration process may not be performed.

Furthermore, in this embodiment, the information of a set of images consisting of the first past image D1 and the second past image D2 is used as the image information. However, the technology of the present disclosure is not limited thereto. Image change information indicating a change in the first past image D1 and the second past image D2 over time may be used as the image information. Here, a medical information acquisition device according to a second embodiment using the image change information as the image information will be described. In addition, since the medical information acquisition device according to the second embodiment has substantially the same configuration as the medical information acquisition device 1 according to the first embodiment illustrated in FIG. 2, the detailed description thereof will be omitted here, and only different portions will be described.

Figure 10:
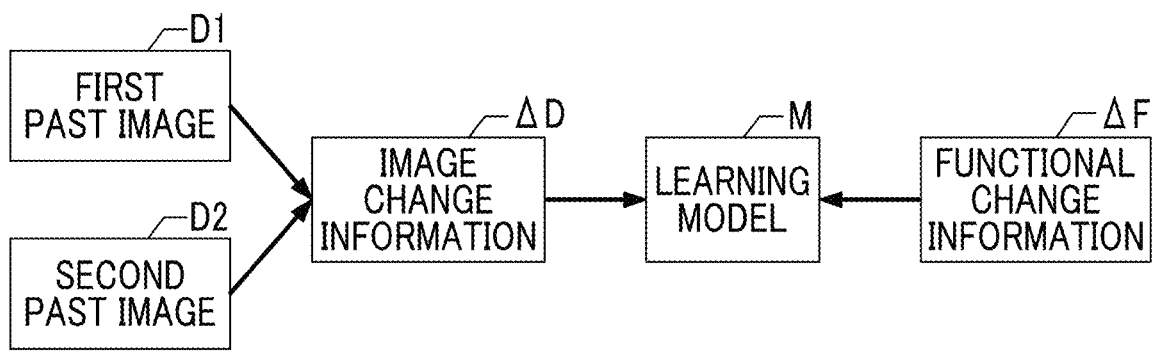
FIG. 10 is a diagram illustrating a second method for training the learning model.

FIG. 10 is a diagram illustrating a second method for training the learning model M. In the second embodiment, as illustrated in FIG. 10, the learning unit 23 inputs a difference image between the first past image D1 and the second past image D2 as image change information ΔD to the learning model M. The difference image is generated by calculating the absolute value of a difference value between the corresponding pixels of the first past image D1 and the second past image D2 that have been subjected to the density normalization process and the registration process by the image processing unit 22. In addition, a method for generating the difference image is not limited to the above, and the difference image can be generated by a known method.

Then, the learning unit 23 inputs the image change information ΔD and the functional change information ΔF which is the amount of change in the value of the second score F2 with respect to the value of the first score F1 as the training data to the learning model M to train the learning model M, that is, to perform machine learning. The learning is performed in this way to generate the trained model 24 that receives, as an input, the image change information ΔD which is the difference image between the images of the same subject captured at different times and obtains the functional change information ΔF.

Figure 11:
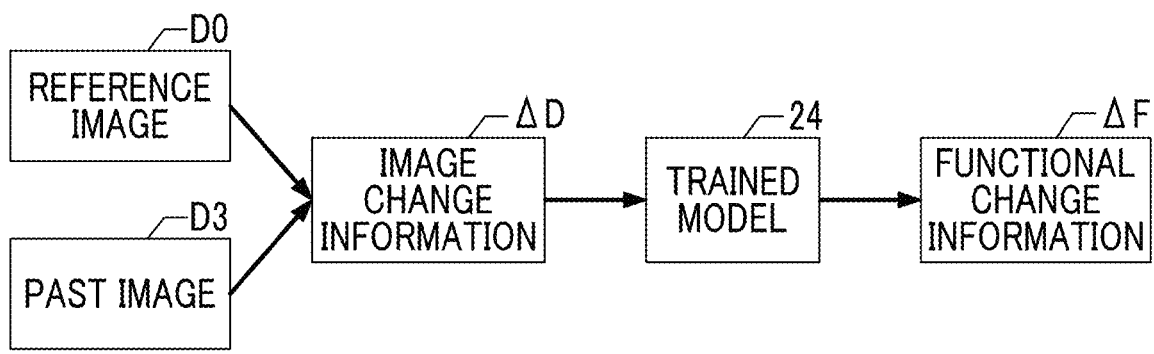
FIG. 11 is a diagram illustrating the acquisition of functional change information by an information acquisition unit according to a second embodiment of the present disclosure.

FIG. 11 is a diagram illustrating the acquisition of the functional change information ΔF by the information acquisition unit 21 in the second embodiment of the present disclosure. As illustrated in FIG. 11, the information acquisition unit 21 acquires the functional change information ΔF output from the trained model 24 trained as described above in a case in which a difference image between the reference image D0 and the past image D3 is input as the image change information ΔD to the trained model 24, that is, the amount of change in the value of the future score F3 with respect to the value of the reference score F0. In addition, the information acquisition unit 21 acquires, as the future score F3, a score obtained by adding the acquired functional change information ΔF to the reference score F0.

As described above, since the image information input to the learning model M and the trained model 24 is the difference image, that is, the image change information ΔD, the learning model M and the trained model 24 do not need to extract the change information between the first past image D1 and the second past image D2 as a feature and can more explicitly learn the change information.

In the second embodiment, the difference image is used as the image change information ΔD. However, the technology of the present disclosure is not limited thereto. For example, the volume of the entire brain may be calculated in each of the first past image D1, the second past image D2, the reference image D0, and the past image D3. Then, a change in the volume of the brain, that is, the atrophy rate of the brain may be calculated in the first past image D1 and the second past image D2 and in the reference image D0 and the past image D3. Then, the change in the volume of the brain may be used as the image change information ΔD. In addition, the change in the volume of the brain may not be a change in the volume of the entire brain. For example, the brain may be divided by a predetermined method in each image, and the volume of each area may be calculated. Then, a change in the volume of a predetermined area may be used as the image change information ΔD.

The medical information acquisition device according to the second embodiment can acquire the functional change information ΔF, similarly to the medical information acquisition device according to the first embodiment. Therefore, the acquisition of the functional change information ΔF makes it possible to acquire the score obtained by adding the acquired functional change information ΔF to the reference score F0 as the future score F3. As a result, the degree of progression of dementia can be predicted to support the diagnosis of dementia.

Next, a medical information acquisition device according to a third embodiment will be described. In addition, since the medical information acquisition device according to the third embodiment has substantially the same configuration as the medical information acquisition device 1 according to the first embodiment illustrated in FIG. 2, the detailed description thereof will be omitted here, and only different portions will be described.

Figure 12:
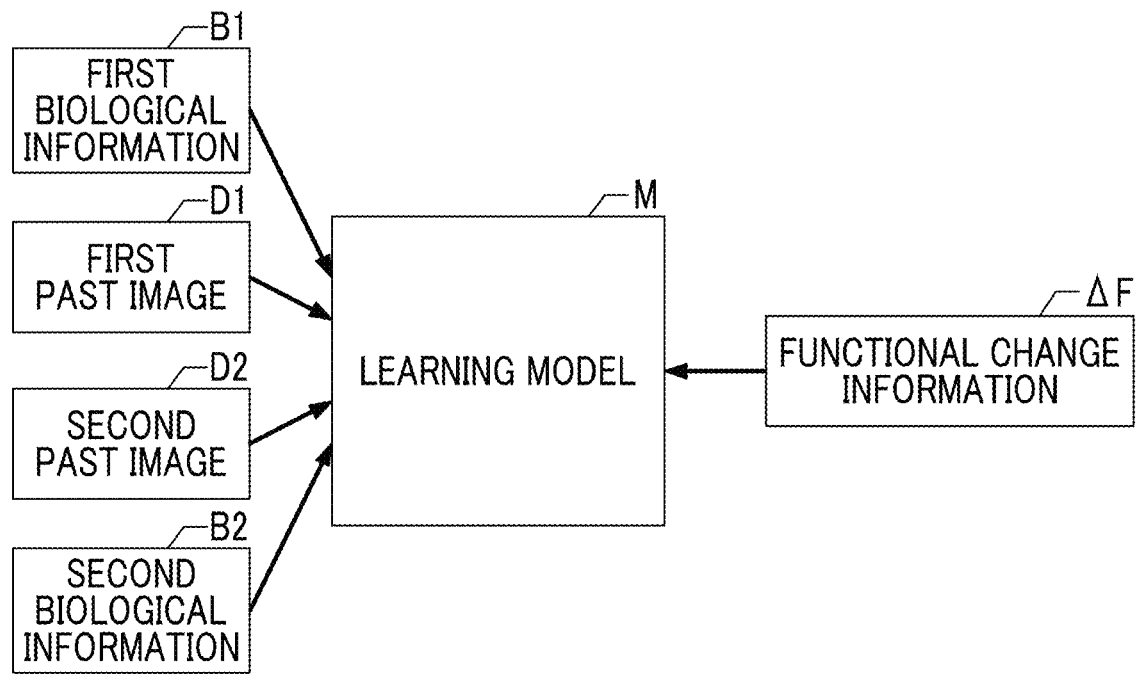
FIG. 12 is a diagram illustrating a third method for training the learning model.

FIG. 12 is a diagram illustrating a third method for training the learning model M. In the third embodiment, the information acquisition unit 21 acquires biological information based on first biological information B1 acquired by biopsy on the subject at the first time tp1 and second biological information B2 acquired by biopsy on the subject at the second time tp2, in addition to the image information which is the information of a set of images consisting of the first past image D1 and the second past image D2. Here, the biopsy includes one or more examinations, such as a blood examination and a cerebrospinal fluid (CSF) examination. In the third embodiment, both the blood examination and the cerebrospinal fluid examination are performed as the biopsy. However, the technology of the present disclosure is not limited thereto. Only one of the examinations may be performed. In addition, the first biological information B1 and the second biological information B2 are information of the examination results acquired by the above-described examinations.

For example, the amount of amyloid beta peptide-related proteins that are considered to damage nerve cells in the blood can be examined to predict the possibility of mild cognitive impairment (MCI) at an earlier stage than the onset of dementia symptoms. Therefore, as the training data to be input to the learning model M, the amount of proteins is used as the first biological information B1 and the second biological information B2 to train the learning model M using change information between the first biological information B1 and the second biological information B2, that is, change information of the amount of proteins as a feature.

In addition, it is known that amyloid beta 42 in the cerebrospinal fluid is reduced from nearly 10 years before the onset of Alzheimer-type dementia. Therefore, a change in the amount of amyloid beta 42 in the cerebrospinal fluid can be examined to predict the possibility of developing Alzheimer-type dementia 10 years later. In addition, it is known that the volume of the brain increases as the amount of cerebrospinal fluid increases. For this reason, a change in the amount of cerebrospinal fluid can be examined to detect the volume of the brain, that is, the atrophy rate of the brain. Therefore, as the training data to be input to the learning model M, the amount of amyloid beta 42 and the amount of cerebrospinal fluid are used as the first biological information B1 and the second biological information B2 to train the learning model M using the change information between the first biological information B1 and the second biological information B2, that is, the change information of the amount of amyloid beta 42 and the amount of cerebrospinal fluid as a feature.

Figure 13:
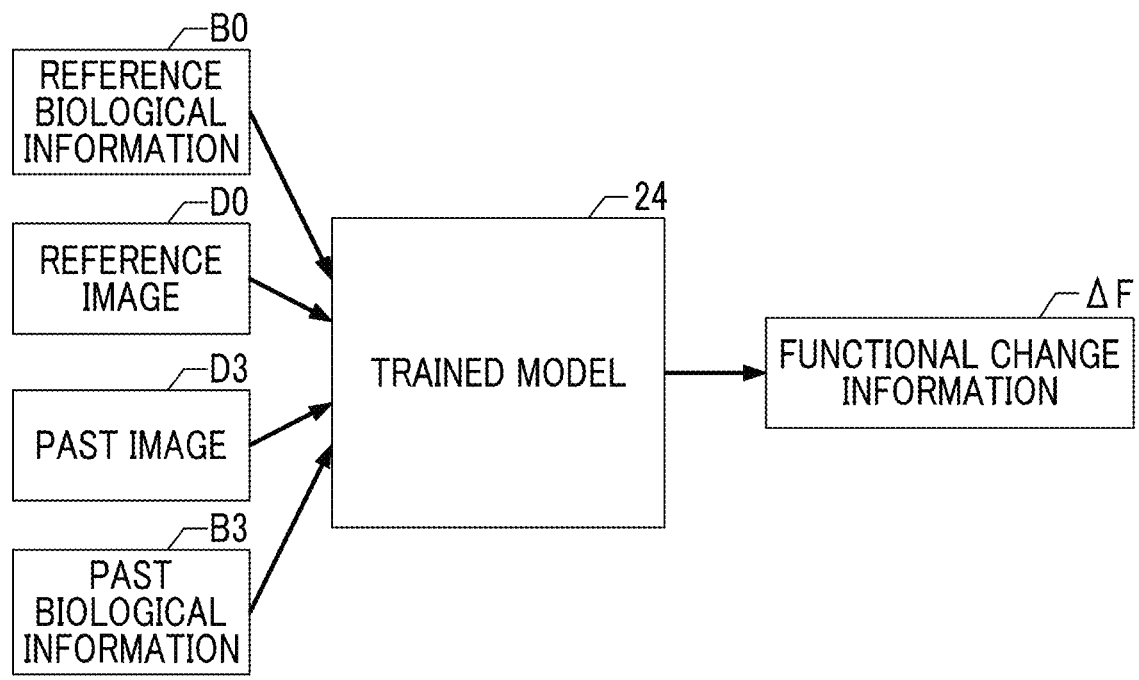
FIG. 13 is a diagram illustrating the acquisition of functional change information by an information acquisition unit according to a third embodiment of the present disclosure.

FIG. 13 is a diagram illustrating the acquisition of the functional change information ΔF by the information acquisition unit 21 according to the third embodiment of the present disclosure. As illustrated in FIG. 13, the information acquisition unit 21 acquires the functional change information ΔF output from the trained model 24 trained as described above in a case in which the reference image D0, the past image D3, past biological information B3 acquired by biopsy on the subject at the second time tp2, and reference biological information B0 acquired by biopsy on the subject at the reference time t0 are input to the trained model 24, that is, the amount of change in the value of the future score F3 with respect to the value of the reference score F0. In addition, the information acquisition unit 21 acquires, as the future score F3, a score obtained by adding the acquired functional change information ΔF to the reference score F0.

As described above, the trained model 24 learns the change information between the first biological information B1 and the second biological information B2, that is, the change information of the amount of proteins and the change information of the amount of amyloid beta 42 and the amount of cerebrospinal fluid as a feature. Therefore, not only the image information but also the change information between the first biological information B1 and the second biological information B2, that is, the change information of the amount of proteins and the change information of the amount of amyloid beta 42 and the amount of cerebrospinal fluid are reflected in the functional change information ΔF output from the trained model 24. As a result, the accuracy of predicting the degree of progression of dementia is improved.

In the third embodiment, as illustrated in FIG. 13, in addition to the reference image D0 and the past image D3, the past biological information B3 and the reference biological information B0 are input to the trained model 24. However, the technology of the present disclosure is not limited thereto. Even in a case in which only the reference image D0 and the past image D3 are input to the trained model 24, the information acquisition unit 21 can acquire the functional change information ΔF. However, the configuration in which the past biological information B3 and the reference biological information B0 are also input to the trained model 24 can further improve the accuracy of predicting the degree of progression of dementia.

Next, a medical information acquisition device according to a fourth embodiment will be described. In addition, since the medical information acquisition device according to the fourth embodiment has substantially the same configuration as the medical information acquisition device according to the second embodiment and the medical information acquisition device according to the third embodiment, the detailed description thereof will be omitted here, and only different portions will be described.

Figure 14:
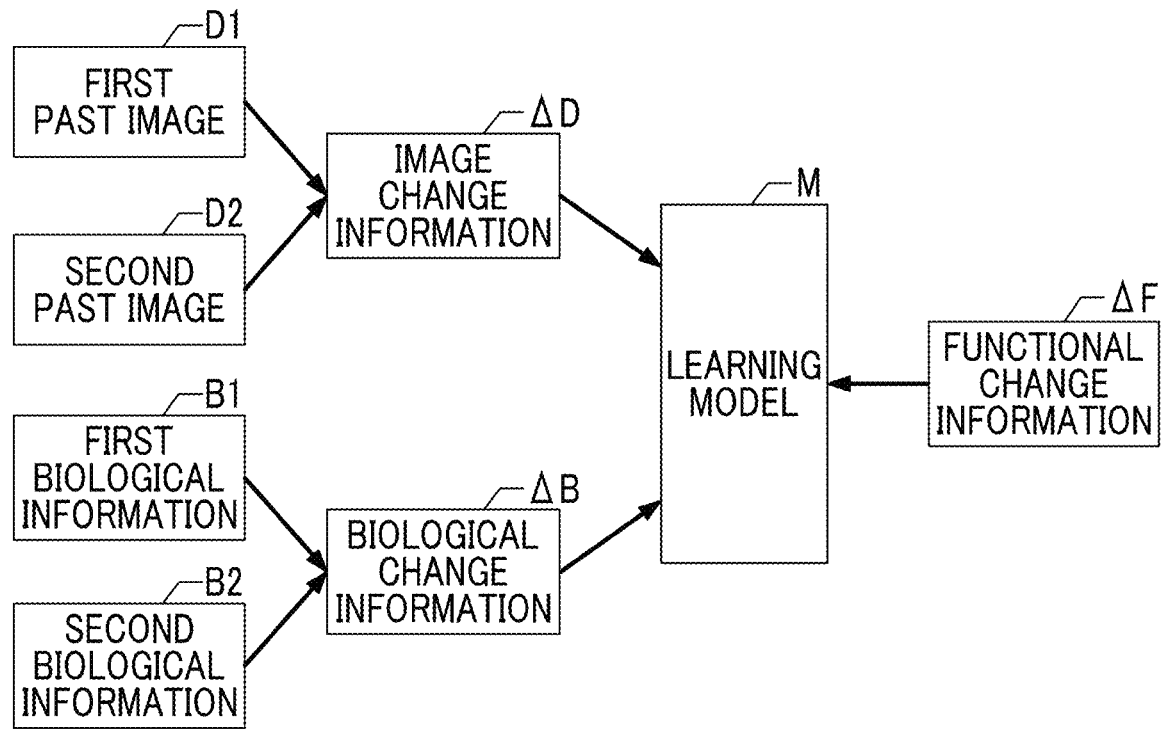
FIG. 14 is a diagram illustrating a fourth method for training the learning model.

FIG. 14 is a diagram illustrating a third method for training the learning model M. As illustrated in FIG. 14, the learning unit 23 inputs the difference image between the first past image D1 and the second past image D2 as the image change information ΔD to the learning model M. Further, the learning unit 23 inputs the change information between the first biological information B1 and the second biological information B2, that is, the change information of the amount of proteins and the change information of the amount of amyloid beta 42 as biological change information ΔB to the learning model M.

Then, the learning unit 23 inputs the image change information ΔD, the biological change information ΔB, and the functional change information ΔF which is the amount of change in the value of the second score F2 with respect to the value of the first score F1 as the training data to the learning model M to train the learning model M, that is, to perform machine learning. The learning is performed in this way to generate the trained model 24 that receives, as an input, the image change information ΔD which is the difference image between the images of the same subject captured at different times and the biological change information ΔB which is the change information of the amount of proteins and the change information of the amount of amyloid beta 42 acquired by biopsy on the same subject at the different times and obtains the functional change information ΔF.

Figure 15:
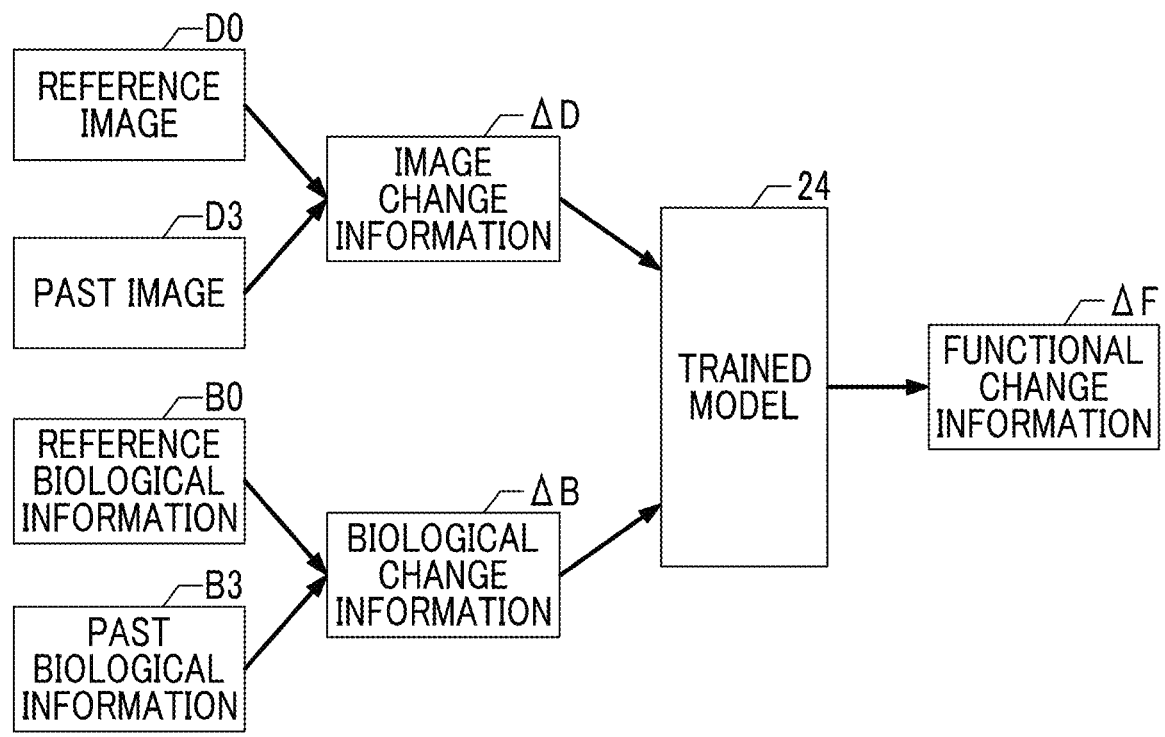
FIG. 15 is a diagram illustrating the acquisition of functional change information by an information acquisition unit according to a fourth embodiment of the present disclosure.

FIG. 15 is a diagram illustrating the acquisition of the functional change information ΔF by the information acquisition unit 21 according to the fourth embodiment of the present disclosure. As illustrated in FIG. 15, the information acquisition unit 21 acquires the functional change information ΔF output from the trained model 24 trained as described above in a case in which the difference image between the reference image D0 and the past image D3 is input as the image change information ΔD to the trained model 24 and biological change information ΔB which is change information between the past biological information B3 acquired by biopsy on the subject at the second time tp2 and the reference biological information B0 acquired by biopsy on the subject at the reference time t0 is input to the trained model 24, that is, the amount of change in the value of the future score F3 with respect to the value of the reference score F0. In addition, the information acquisition unit 21 acquires, as the future score F3, a score obtained by adding the acquired functional change information ΔF to the reference score F0.

As described above, since the image change information ΔD and the biological change information ΔB are used as the image information and the biological information input to the learning model M and the trained model 24, respectively, the learning model M and the trained model 24 do not need to extract the change information between the first past image D1 and the second past image D2, the change information of the amount of proteins, and the change information of the amount of amyloid beta 42 as features and can explicitly learn the change information.

Further, in the fourth embodiment, as illustrated in FIG. 15, in addition to the image change information ΔD, the biological change information ΔB is input to the trained model 24. However, the technology of the present disclosure is not limited thereto. Even in a case in which only the image change information ΔD is input to the trained model 24, the information acquisition unit 21 can acquire the functional change information ΔF. However, the configuration in which the biological change information ΔB is also input to the trained model 24 can further improve the accuracy of predicting the degree of progression of dementia.

Next, a medical information acquisition device according to a fifth embodiment will be described. In addition, since the medical information acquisition device according to the fifth embodiment has substantially the same configuration as the medical information acquisition device according to the first embodiment, the detailed description thereof will be omitted here, and only different portions will be described.

Figure 16:
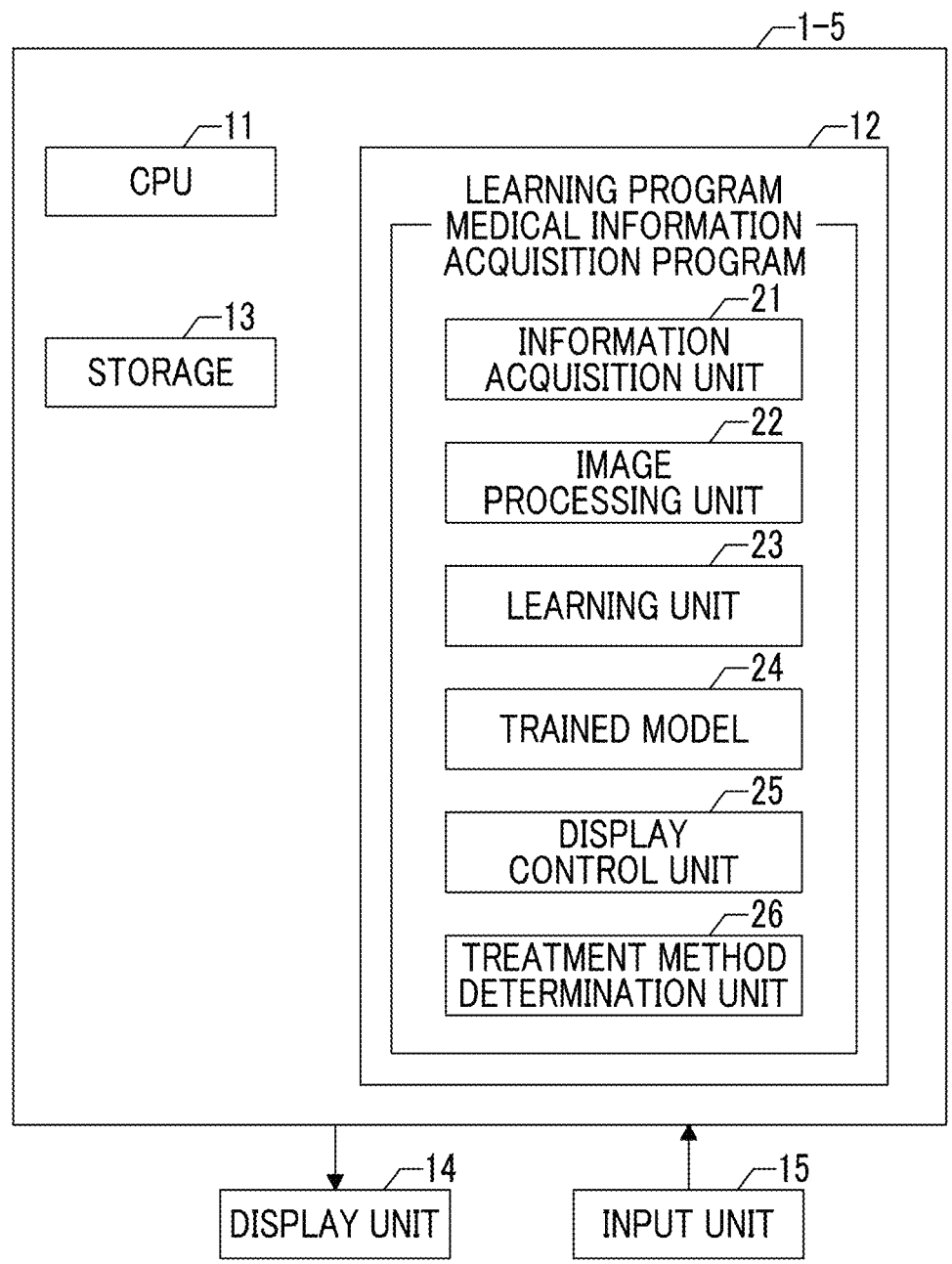
FIG. 16 is a block diagram schematically illustrating the configuration of a medical information acquisition device according to a fifth embodiment of the present disclosure.

FIG. 16 is a block diagram schematically illustrating the configuration of a medical information acquisition device 1-5 according to the fifth embodiment of the present disclosure. As illustrated in FIG. 16, the medical information acquisition device 1-5 further comprises a treatment method determination unit 26 as compared to the medical information acquisition device 1 according to the first embodiment illustrated in FIG. 2. The treatment method determination unit 26 determines a treatment method to be performed on the subject on the basis of the functional change information ΔF acquired by the information acquisition unit 21. Specifically, as illustrated in FIG. 7, for example, the amount of drug to be administered to a target patient who is the subject, the type of drug, and whether or not to perform a treatment are determined in each of a case in which there is a possibility of severe dementia, a case in which there is a possibility of intermediate dementia, and a case in which there is a possibility of mild dementia, according to the prediction result of dementia based on the functional change information ΔF.

Specifically, the treatment method determination unit 26 uses machine learning to derive a treatment method from the functional change information ΔF acquired by the information acquisition unit 21. For example, it is possible to propose a more effective treatment method to the patient using the trained model subjected to machine learning using, as training data, information indicating that, as a result of administering three tablets of drug A daily to the patient whose functional change information ΔF was −10 points in the past, the progression of dementia subsided. In this embodiment, the treatment method determination unit 26 derives the treatment method from the functional change information ΔF. However, the treatment method may be derived from the future score F3. In addition, the treatment method determination unit 26 may use, for example, a correspondence table or a correspondence expression between the functional change information ΔF or the future score F3 and the treatment method as long as it can derive the treatment method, instead of machine learning.

Next, a medical information acquisition device according to a sixth embodiment will be described. In addition, since the medical information acquisition device according to the sixth embodiment has substantially the same configuration as the medical information acquisition device according to the first embodiment, the detailed description thereof will be omitted here, and only different portions will be described.

Figure 17:
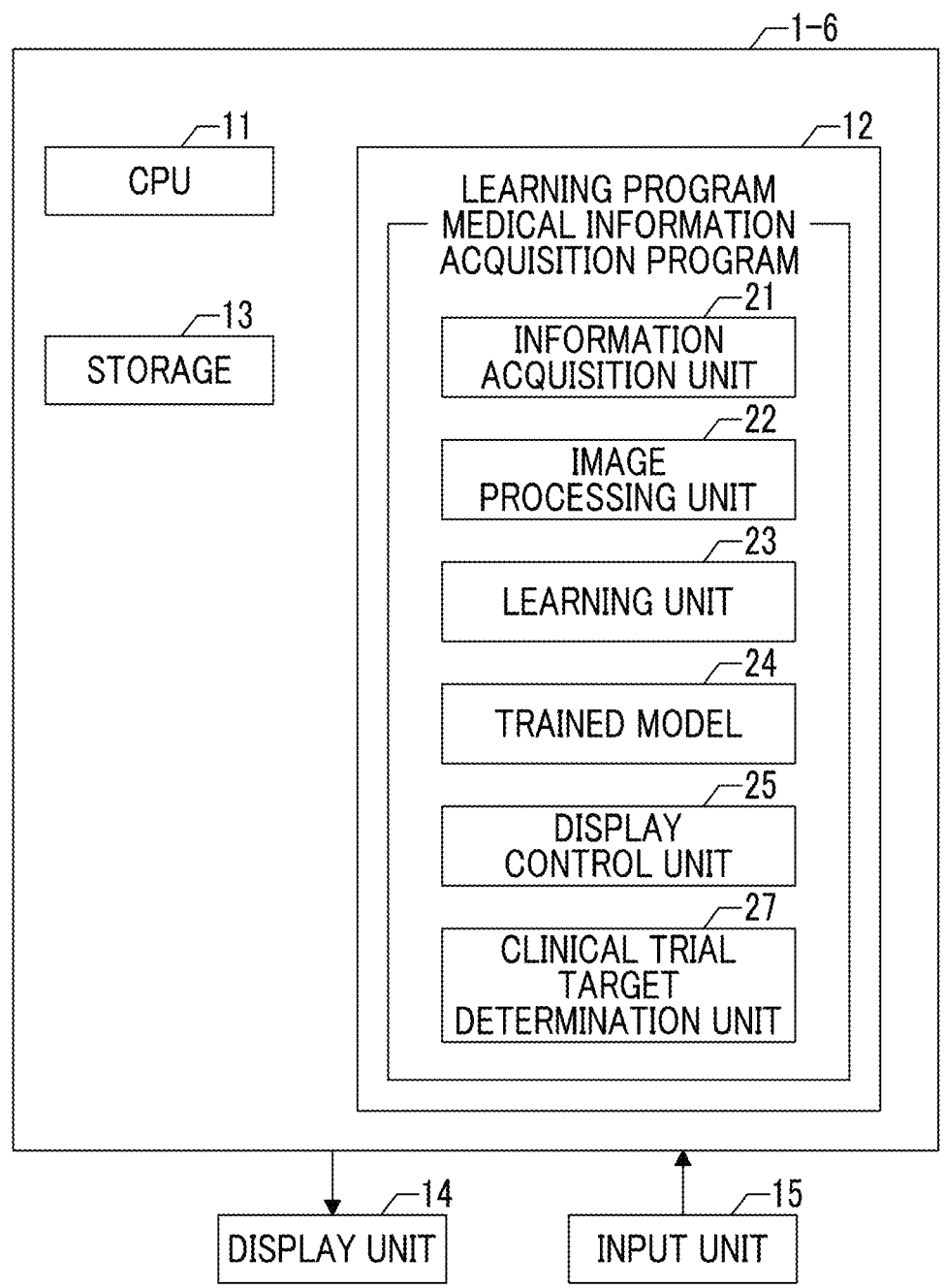
FIG. 17 is a block diagram schematically illustrating the configuration of a medical information acquisition device according to a sixth embodiment of the present disclosure.

FIG. 17 is a block diagram schematically illustrating the configuration of a medical information acquisition device 1-6 according to the sixth embodiment of the present disclosure. As illustrated in FIG. 17, the medical information acquisition device 1-6 further comprises a clinical trial target determination unit 27, as compared to the medical information acquisition device 1 according to the first embodiment illustrated in FIG. 2. The clinical trial target determination unit 27 determines whether or not the subject is suitable for a clinical trial on the basis of the functional change information ΔF acquired by the information acquisition unit 21. For example, as illustrated in FIG. 7, in a case in which the prediction result of dementia based on the functional change information ΔF indicates that the subject is normal, a target patient who is the subject is highly likely not to have dementia. In other words, it is difficult to determine whether or not the drug is effective even in a case in which the drug is administered. Therefore, the subject is not preferable as the clinical trial target. Therefore, in a case in which the prediction result of dementia based on the functional change information ΔF indicates that the subject is normal, the clinical trial target determination unit 27 determines that the target patient who is the subject is not the clinical trial target.

On the other hand, in a case in which the prediction result of dementia based on the functional change information ΔF indicates that the subject has severe dementia, the target patient who is the subject is likely to have dementia. That is, it is easy to determine whether or not the drug is effective in a case in which the drug is administered, that is, whether or not the progression of dementia can be slowed down. Therefore, the patient is preferable as the clinical trial target. Therefore, in a case in which the prediction result of dementia based on the functional change information ΔF indicates that the subject has severe dementia, the clinical trial target determination unit 27 determines that the target patient who is the subject is the clinical trial target.

Further, in this embodiment, in a case in which the prediction result of dementia based on the functional change information ΔF indicates that there is a possibility of intermediate dementia, the target patient who is the subject is determined to be the clinical trial target. In a case in which the prediction result indicates that there is a possibility of mild dementia, the target patient who is the subject is determined not to be the clinical trial target. In addition, in a case in which the prediction result of dementia based on the functional change information ΔF indicates that there is a possibility of intermediate dementia or that there is a possibility of mild dementia, it is possible to appropriately change the determination of whether or not the patent is the clinical trial target, according to, for example, the content of the clinical trial.

In this embodiment, the clinical trial target determination unit 27 determines the clinical trial target from the prediction results illustrated in FIG. 7. However, the clinical trial method may be derived from the future score F3 and the functional change information ΔF.

Next, a medical information acquisition device according to a seventh embodiment will be described. In addition, since the medical information acquisition device according to the seventh embodiment has substantially the same configuration as the medical information acquisition device according to the first embodiment, the detailed description thereof will be omitted here, and only different portions will be described.

Figure 18:
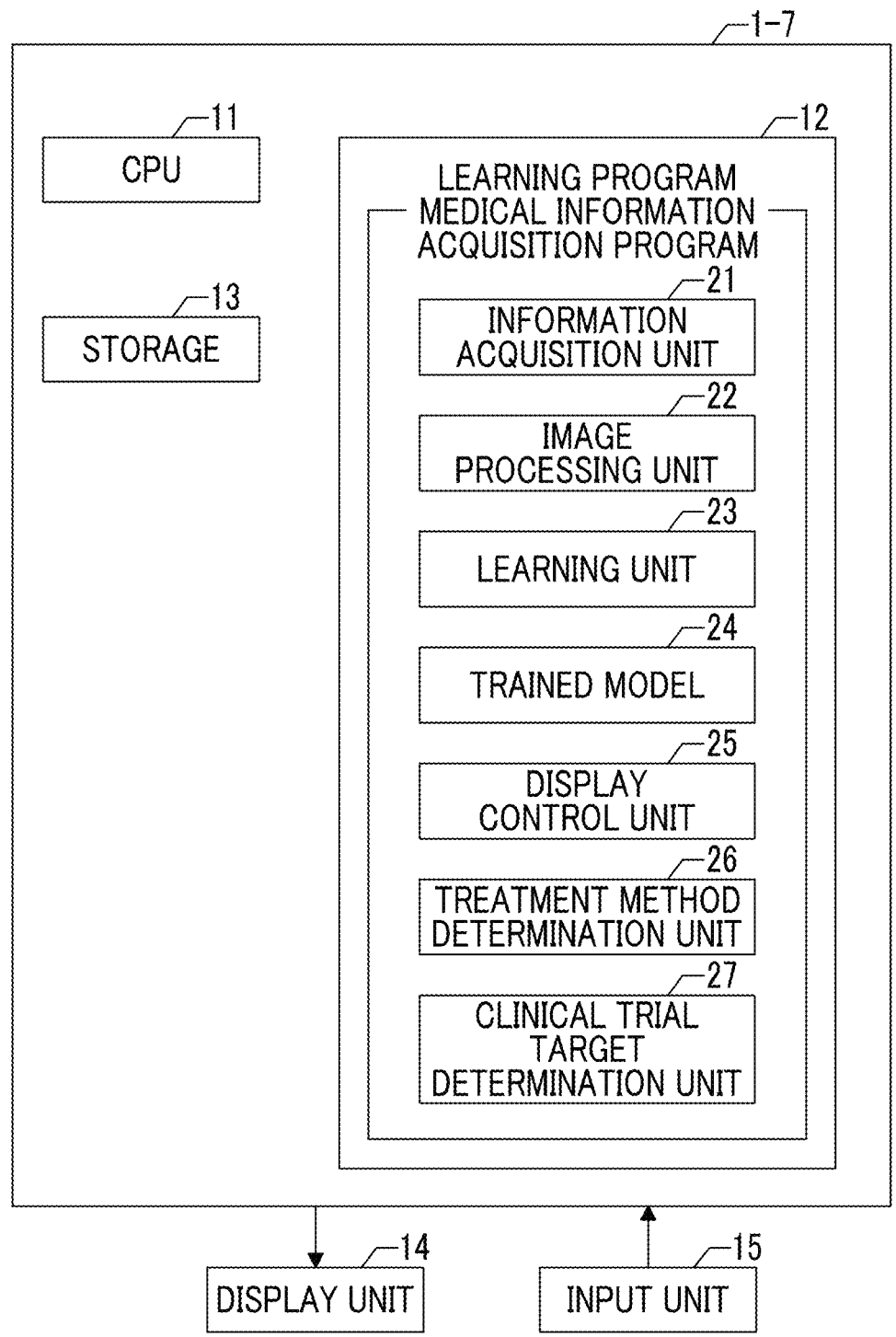
FIG. 18 is a block diagram schematically illustrating the configuration of a medical information acquisition device according to a seventh embodiment of the present disclosure.

FIG. 18 is a block diagram schematically illustrating the configuration of a medical information acquisition device 1-7 according to the seventh embodiment of the present disclosure. As illustrated in FIG. 18, the medical information acquisition device 1-7 further comprises a treatment method determination unit 26 and a clinical trial target determination unit 27, as compared to the medical information acquisition device 1 according to the first embodiment illustrated in FIG. 2. In addition, the treatment method determination unit 26 is the same as the treatment method determination unit 26 of the medical information acquisition device 1-5 according to the fifth embodiment, and the clinical trial target determination unit 27 is the same as the clinical trial target determination unit 27 of the medical information acquisition device 1-6 according to the sixth embodiment. Therefore, the description thereof will be omitted here.

In the above-described embodiments, the reference functional information (for example, the reference score F0) acquired at the reference time t0 and the past functional information (for example, the second score F2) acquired at the second time tp3 may be used as the data to be input to the trained model 24. In this case, it is possible to improve the accuracy of the functional change information ΔF output from the trained model 24.

Further, in the above-described embodiments, the diffusion-weighted images of the MRI images are used as the first and second past images D1 and D2, the past image D3, and the reference image D0. However, MRI images other than the diffusion-weighted images may be used. For example, fluid-attenuated inversion recovery (FLAIR) images, T1-weighted images, and T2-weighted images may be used. In addition, one or more images selected from the diffusion-weighted image, the FLAIR image, the T1-weighted image, the T2-weighted image, and the like may be used. Further, instead of the MRI image, a non-contrast-enhanced CT image and a contrast-enhanced CT image may be used, or other medical images, such as PET images, may be used. Furthermore, two or more types of images among the above-mentioned types of images may be used. For example, in a case in which both the contrast-enhanced CT image and the non-contrast-enhanced CT image are used for training the learning model M, it is possible to acquire the functional change information ΔF even though the CT image from which the degree of progression of dementia is predicted is any one of the contrast-enhanced CT image or the non-contrast-enhanced CT image.

Further, in the above-described embodiments, as the score, the score acquired by the psychological examination for dementia is used. However, the technology of the present disclosure is not limited thereto. For example, a score acquired by a psychological examination for developmental disorders may be used, or any score may be used as long as it is acquired by a psychological examination for the brain function that is related to the change information of the brain image.

Furthermore, in the above-described embodiments, the brain images are used as the first and second past images D1 and D2, the past image D3, and the reference image D0. However, the technology of the present disclosure is not limited thereto. For example, the medical images of the chest, abdomen, whole body, and limbs of the human body may be used. For example, in a case in which a three-dimensional image of the bone of the subject is acquired, a score acquired in a checklist for evaluating the health of the bone is used as the score. This makes it possible to predict the degree of weakness of the bone.

Moreover, in the above-described embodiments, the score acquired by the psychological examination is used as the functional change information. However, the biopsy result obtained by biopsy may be used as the functional change information. Specifically, in a case in which the information acquisition unit 21 acquires the three-dimensional image of the bone of the subject instead of the brain image, for example, bone density may be measured by applying ultrasonic waves to the bones of the heel and shin to measure the amount of minerals, such as calcium, in the bones, and the measurement result may be used as the score. In this case, the information acquisition unit 21 acquires the change information of the bone density output from the trained model 24. This makes it possible to predict the degree of progression of osteoporosis from the change information of the bone density.

In the above-described embodiments, for example, the following various processors can be used as the hardware structure of processing units performing various processes, such as the information acquisition unit 21, the image processing unit 22, the learning unit 23, the trained model 24, the display control unit 25, the treatment method determination unit 26, and the clinical trial target determination unit 27. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

According to a second aspect of the present disclosure, in the trained model according to the first aspect, the image information may be information of a set of images consisting of the first past image and the second past image.

According to a third aspect of the present disclosure, in the trained model according to the first aspect, the image information may be image change information indicating a change between the first past image and the second past image over time.

According to a fourth aspect of the present disclosure, in the trained model according to the first to third aspects, the functional change information may be information indicating a change between a first score acquired by a psychological examination on the subject at the second time and a second score acquired by a psychological examination on the subject at the third time over time.

According to a fifth aspect of the present disclosure, in the trained model according to the first to third aspects, the functional change information may be information indicating a change between a first biopsy result acquired by biopsy on the subject at the second time and a second biopsy result acquired by biopsy on the subject at the third time over time.

According to a sixth aspect of the present disclosure, in the trained model according to the fourth aspect, the first score and the second score may be scores acquired by a psychological examination for dementia.

According to a seventh aspect of the present disclosure, in the trained model according to the first to sixth aspects, the information set may include biological information based on first biological information acquired by biopsy on the subject at the first time and second biological information acquired by biopsy on the subject at the second time. The trained model may have been trained to receive the image information and the biological information as an input and to output the functional change information.

According to an eighth aspect of the present disclosure, there is provided a medical information acquisition device comprising an information acquisition unit that acquires functional change information obtained on the basis of a reference image and a past image acquired by capturing images of the same subject at a reference time and a past time closer to the past than the reference time, respectively, using the trained model according to the first to sixth aspects.

According to a ninth aspect of the present disclosure, there is provided a medical information acquisition device comprising an information acquisition unit that acquires functional change information obtained on the basis of a reference image and a past image acquired by capturing images of the same subject at a reference time and a past time closer to the past than the reference time, respectively, and reference biological information and past biological information acquired by biopsy on the same subject at the reference time and the past time, respectively, using the trained model according to the seventh aspect.

According to a tenth aspect of the present disclosure, the medical information acquisition device according to the eighth and ninth aspects may further comprise an image processing unit that performs at least one of a density normalization process or a registration process on the reference image and the past image, and the first past image and the second past image.

According to an eleventh aspect of the present disclosure, the medical information acquisition device according to the eighth to tenth aspects may further comprise a treatment method determination unit that determines a treatment method to be performed on the subject on the basis of the functional change information acquired by the information acquisition unit.

According to a twelfth aspect of the present disclosure, the medical information acquisition device according to the eighth to eleventh aspects may further comprise a clinical trial target determination unit that determines a drug clinical trial target on the basis of the functional change information acquired by the information acquisition unit.

According to a thirteenth aspect of the present disclosure, there is provided a display device comprising a display unit that displays information acquired by the medical information acquisition device according to the eighth to twelfth aspects. In addition, the display device according to the present disclosure may be provided in the above-described medical information acquisition device.

According to a sixteenth aspect of the present disclosure, there is provided a medical information acquisition method comprising: acquiring functional change information obtained on the basis of a reference image and a past image acquired by capturing images of the same subject at a reference time and a past time closer to the past than the reference time, respectively, using the trained model according to the first to sixth aspects.

According to a seventeenth aspect of the present, there is provided a medical information acquisition method comprising: acquiring functional change information obtained on the basis of a reference image and a past image acquired by capturing images of the same subject at a reference time and a past time closer to the past than the reference time, respectively, and reference biological information and past biological information acquired by biopsy on the same subject at the reference time and the past time, respectively, using the trained model according to the seventh aspect.

According to an eighteenth aspect of the present disclosure, there is provided a medical information acquisition program that causes a computer to perform: acquiring functional change information obtained on the basis of a reference image and a past image acquired by capturing images of the same subject at a reference time and a past time closer to the past than the reference time, respectively, using the trained model according to the first to sixth aspects.

According to a nineteenth aspect of the present disclosure, there is provided a medical information acquisition program that causes a computer to perform: acquiring functional change information obtained on the basis of a reference image and a past image acquired by capturing images of the same subject at a reference time and a past time closer to the past than the reference time, respectively, and reference biological information and past biological information acquired by biopsy on the same subject at the reference time and the past time, respectively, using the trained model according to the seventh aspect.

According to the trained model, the learning method, the learning program, the medical information acquisition device, the medical information acquisition method, and the medical information acquisition program of the present disclosure, the degree of progression of a disease can be predicted to support diagnosis.

What is claimed is:

1. A non-transitory computer-readable storage medium storing a trained model that has been trained to receive, by a processor, image information as an input and to output functional change information, using, as training data, learning information including a plurality of information sets each of which includes:
   the image information based on a first past image acquired by capturing an image of a subject at a first time and a second past image acquired by capturing an image of the subject at a second time after the first time; and
   the functional change information that indicates a change in a function of the subject over time and is based on first past functional information acquired by examining the function of the subject at the second time and second past functional information acquired by examining the function of the subject at a third time after the second time.

2. The non-transitory computer-readable storage medium according to claim 1,
   wherein the image information is information of a set of images consisting of the first past image and the second past image.

3. The non-transitory computer-readable storage medium according to claim 1,
   wherein the image information is image change information indicating a change between the first past image and the second past image over time.

4. The non-transitory computer-readable storage medium according to claim 1,
   wherein the functional change information is information indicating a change between a first score acquired by a psychological examination on the subject at the second time and a second score acquired by a psychological examination on the subject at the third time over time.

5. The non-transitory computer-readable storage medium according to claim 4,
   wherein the first score and the second score are scores acquired by a psychological examination for dementia.

6. The non-transitory computer-readable storage medium according to claim 1, wherein the functional change information is information indicating a change between a first biopsy result acquired by biopsy on the subject at the second time and a second biopsy result acquired by biopsy on the subject at the third time over time.

7. The non-transitory computer-readable storage medium according to claim 1,
wherein the information set includes biological information based on first biological information acquired by biopsy on the subject at the first time and second biological information acquired by biopsy on the subject at the second time, and
the trained model has been trained to receive the image information and the biological information as an input and to output the functional change information.

8. A medical information acquisition device comprising:
a processor that acquires functional change information obtained on the basis of a reference image and a past image acquired by capturing images of the same subject at a reference time and a past time before the reference time, respectively, and reference biological information and past biological information acquired by biopsy on the same subject at the reference time and the past time, respectively, using the trained model according to claim 7.

9. A medical information acquisition method comprising:
by a processor, acquiring functional change information obtained on the basis of a reference image and a past image acquired by capturing images of the same subject at a reference time and a past time before the reference time, respectively, and reference biological information and past biological information acquired by biopsy on the same subject at the reference time and the past time, respectively, using the trained model according to claim 7.

10. A medical information acquisition device comprising:
a processor that acquires functional change information obtained on the basis of a reference image and a past image acquired by capturing images of the same subject at a reference time and a past time before the reference time, respectively, using the trained model according to claim 1.

11. The medical information acquisition device according to claim 10, wherein:
the processor further performs at least one of a density normalization process or a registration process on the reference image and the past image, and the first past image and the second past image.

12. The medical information acquisition device according to claim 10, wherein:
the processor further determines a treatment method to be performed on the subject on the basis of the functional change information acquired.

13. The medical information acquisition device according to claim 10, wherein:
the processor further determines a drug clinical trial target on the basis of the functional change information acquired.

14. A display device comprising:
a display unit that displays information acquired by the medical information acquisition device according to claim 10.

15. A medical information acquisition method comprising:
by a processor, acquiring functional change information obtained on the basis of a reference image and a past image acquired by capturing images of the same subject at a reference time and a past time before the reference time, respectively, using the trained model according to claim 1.

16. A non-transitory computer-readable storage medium storing a medical information acquisition program that causes a computer to perform:
acquiring functional change information obtained on the basis of a reference image and a past image acquired by capturing images of a subject at a reference time and a past time before the reference time, respectively, using a trained model that uses, as training data, learning information including a plurality of information sets each of which includes:
image information based on a first past image acquired by capturing an image of the subject at a first time and a second past image acquired by capturing an image of the subject at a second time after the first time; and
functional change information that indicates a change in a function of the subject over time and is based on first past functional information acquired by examining the function of the subject at the second time and second past functional information acquired by examining the function of the subject at a third time after the second time,
wherein the trained model has been trained to receive the image information as an input and to output the functional change information.

17. A non-transitory computer-readable storage medium storing a medical information acquisition program that causes a computer to perform:
acquiring functional change information obtained on the basis of a reference image and a past image acquired by capturing images of a subject at a reference time and a past time before the reference time, respectively, and reference biological information and past biological information acquired by biopsy on the subject at the reference time and the past time, respectively, using a trained model that uses, as training data, learning information including a plurality of information sets each of which includes:
image information based on a first past image acquired by capturing an image of the subject at a first time and a second past image acquired by capturing an image of the subject at a second time after the first time; and
functional change information that indicates a change in a function of the subject over time and is based on first past functional information acquired by examining the function of the subject at the second time and second past functional information acquired by examining the function of the subject at a third time after the second time; and
biological information based on first biological information acquired by biopsy on the subject at the first time and second biological information acquired by biopsy on the subject at the second time, and
wherein the trained model has been trained to receive the image information and the biological information as an input and to output the functional change information.

18. A method for training a learning model, the method comprising:
by a processor,
acquiring a plurality of information sets each of which includes image information based on a first past image acquired by capturing an image of a subject at a first time and a second past image acquired by capturing an image of the subject at a second time after the first time and functional change information that indicates a change in a function of the subject over time and is based on first past functional information acquired by examining the function of the subject at the second time and second past functional information acquired by examining the function of the subject at a third time after the second time; and training the learning model, using learning information including the plurality of acquired information sets as training data, to receive the image information as an input and to output the functional change information.

19. A non-transitory computer-readable storage medium storing a program for training a learning model, the program causing a computer to perform:

acquiring a plurality of information sets each of which includes image information based on a first past image acquired by capturing an image of a subject at a first time and a second past image acquired by capturing an image of the subject at a second time after the first time and functional change information that indicates a change in a function of the subject over time and is based on first past functional information acquired by examining the function of the subject at the second time and second past functional information acquired by examining the function of the subject at a third time after the second time; and training the learning model, using learning information including the plurality of acquired information sets as training data, to receive the image information as an input and to output the functional change information.

* * * * *